United States Patent [19]

Ashjian et al.

[11] Patent Number: 5,034,563

[45] Date of Patent: Jul. 23, 1991

[54] NAPHTHALENE ALKYLATION PROCESS

[75] Inventors: Henry Ashjian, East Brunswick; Quang N. Le, Cherry Hill; David O. Marler, Deptford; Joosup Shim, Wenonah; Stephen S. Wong, Medford, all of N.J.

[73] Assignee: Mobil Oil Corporation, Fairfax, Va.

[21] Appl. No.: 505,392

[22] Filed: Apr. 6, 1990

[51] Int. Cl.$^5$ .......................... C07C 2/64; C07C 2/68
[52] U.S. Cl. .................................. 585/455; 585/467
[58] Field of Search ............................. 585/455, 467

[56] References Cited

U.S. PATENT DOCUMENTS

| | | | |
|---|---|---|---|
| 3,929,672 | 12/1975 | Ward | 252/455 Z |
| 4,211,665 | 7/1980 | Pellegrini, Jr. | 252/63 |
| 4,238,343 | 12/1980 | Pellegrini, Jr. | 585/24 |
| 4,570,027 | 2/1986 | Boucher et al. | 585/455 |
| 4,604,491 | 8/1986 | Dressler et al. | 585/26 |
| 4,714,794 | 12/1987 | Yoshida et al. | 585/26 |
| 4,876,408 | 10/1989 | Ratcliffe et al. | 585/467 |

OTHER PUBLICATIONS

"An Introduction to Zeolite Molecular Sieves", Dyer, John Wiley and Sons, Ltd., 1988, ISBN 0471919810, pp. 121-122.

*Primary Examiner*—Anthony McFarlane
*Assistant Examiner*—Nhat Phan
*Attorney, Agent, or Firm*—Alexander J. McKillop; Charles J. Speciale; Malcolm D. Keen

[57] ABSTRACT

Long chain alkyl substituted naphthalenes are produced by the alkylation of naphthalene with an olefin or other alkylating agent possessing at least 6 carbon atoms, usually 12 to 20 carbon atoms, in the presence of an alkylation catalyst comprising a zeolite which contains cations having a radius of at least 2.5 Å. Cations of this size may be provided by hydrated cations such as hydrated ammonium, sodium or potassium cations or by organoammonium cations such as tetraalkylammonium cations. The zeolite is usually a large pore size ze USY. The presence of the bulky cations in the zeolite increases the selectivity of the catalyst for the production of long chain mono-alkyl substituted naphthalenes in preference to more highly substituted products.

27 Claims, No Drawings

NAPHTHALENE ALKYLATION PROCESS

FIELD OF THE INVENTION

This invention relates to the production of alkylated naphthalenes and substituted naphthalenes.

BACKGROUND OF THE INVENTION

Alkylaromatic fluids have been proposed for use as certain types of functional fluids where good thermal and oxidative are required. For example, U.S. Pat. No. 4,714,794 (Yoshida) describes the monoalkylated naphthalenes as having excellent thermal and oxidative stability, low vapor pressure and flash point, good fluidity and high heat transfer capacity and other properties which render them suitable for use as thermal medium oils. The use of a mixture of monoalkylated and polyalkylated naphthalenes as a base for synthetic functional fluids is described in U.S. Pat. No. 4,604,491 (Dressler) and Pellegrini U.S. Pat. Nos. 4,211,665 and 4,238,343 describe the use of alkylaromatics as transformer oils.

The alkylated naphthalenes are usually produced by the alkylation of naphthalene or a substituted naphthalene in the presence of an acidic alkylation catalyst such as a Friedel-Krafts catalyst, for example, an acidic clay as described in Yoshida U.S. Pat. No. 4,714,794 or Dressler U.S. Pat. No. 4,604,491 or a Lewis acid such as aluminum trichloride as described in Pellegrini U.S. Pat. Nos. 4,211,665 and 4,238,343. The use of a catalyst described as a collapsed silica-alumina zeolite as the catalyst for the alkylation of aromatics such as naphthalene is disclosed in Boucher U.S. Pat. No. 4,570,027. The use of various zeolites including intermediate pore size zeolites such as ZSM-5 and large pore size zeolites such as zeolite L and ZSM-4 for the alkylation of various monocyclic aromatics such as benzene is disclosed in Young U.S. Pat. No. 4,301,316.

In the formulation of functional fluids based on the alkyl naphthalenes, it has been found that the preferred alkyl naphthalenes are the mono-substituted naphthalene since they provide the best combination of properties in the finished product: because the mono-alkylated naphthalenes posses fewer benzylic hydrogens than the corresponding di-substituted or polysubstituted versions, they have better oxidative stability and therefore form better functional fluids and additives. In addition, the mono-substituted naphthalenes have a kinematic viscosity in the desirable range of about 5-8 cSt (at 100° C.) when working with alkyl substituents of about 14 to 18 carbon atoms chain length. Although the mono-alkylated naphthalenes may be obtained in admixture with more highly alkylated naphthalenes using conventional Friedel-Krafts catalysts such as those mentioned above or by the use of zeolites such as USY, the selectivity to the desired mono-alkylated naphthalenes is not obtained.

SUMMARY OF THE INVENTION

We have now found that zeolite catalysts can be effective for the production of mono-alkylated naphthalenes and that good selectivity for the mono-substituted naphthalenes may be obtained by the incorporation of cations having a radius of at least 2.5 Å in large pore size zeolites such as zeolite Y. The presence of bulky cations of this type provides good selectivity for the more highly desired mono-alkylated products.

According to the present invention, therefore, we provide a process for the selective production of mono-alkylated naphthalenes and substituted naphthalenes by the alkylation of a naphthalene in the presence of an alkylation catalyst comprising a large pore size zeolite containing a cation having a radius of at least 2.5 Å. Cations conforming to this ionic size requirement include a number of hydrated metal cations as well as certain organic cations, as described below.

DETAILED DESCRIPTION

The starting materials for the production of the alkylated naphthalenes are naphthalene itself as well the substituted naphthalenes which may contain one or more short chain alkyl groups containig up to about eight carbon atoms, such as methyl, ethyl or propyl. Suitable alkyl-substituted naphthalenes include alpha-methylnaphthalene, dimethylnaphthalene and ethylnaphthalene. Naphthalene itself is preferred since the resulting mono-alkylated products have better thermal and oxidative stability than the more highly alkylated materials for the reasons set out above.

The alkylating agents which are used to alkylate the naphthalene include any aliphatic or aromatic organic compound having one or more available alkylating aliphatic groups capable of alkylating the naphthalene. The alkylatable group itself should have at least about 6 carbon atoms, preferably at least about 8, and still more preferably at least about 12 carbon atoms. For the production of functional fluids and additives, the alkyl groups on the alkyl-naphthalene preferably have from about 12 to 30 carbon atoms, with particular preference to about 14 to 18 carbon atoms. A preferred class of alkylating agents are the olefins with the requisite number of carbon atoms, for example, the hexenes, heptenes, octenes, nonenes, decenes, undecenes, dodecenes. Mixtures of the olefins, e.g. mixtures of $C_{12}$–$C_{20}$ or $C_{14}$–$C_{18}$ olefins, are useful. Branched alkylating agents, especially oligomerized olefins such as the trimers, tetramers, pentamers, etc., of light olefins such as ethylene, propylene, the butylenes, etc., are also useful. Other useful alkylating agents which may be used, although less easily, include alcohols (inclusive of monoalcohols, dialcohols, trialcohols, etc.) such as hexanols, heptanols, octanols, nonanols, decanols, undecanols and dodecanols; and alkyl halides such as hexyl chlorides, octyl chlorides, dodecyl chlorides; and higher homologs.

The alkylation reaction between the naphthalene and the alkylating agent is carried out in the presence of a zeolite catalyst which contains a cation of certain specified radius. The molecular size of the alkylation products will require a relatively large pore size in the zeolite in order for the products to leave the zeolite, indicating the need for a relatively large pore size in the zeolite, which will also tent to reduce diffusion limitations with the long chain alkylating agents. The large pore size zeolites are the most useful zeolite catalysts for this purpose although the less highly constrained intermediate pore size zeolites may also be used, as discussed below. The large pore size zeolites are zeolites such as faujasite, the synthetic faujasites (zeolites X and Y), zeolite L, ZSM-4, ZSM-18, ZSM-20, mordenite and offretite which are generally useful for this purpose are characterised by the presence of a 12-membered oxygen ring system in the molecular structure and by the existence of pores with a minimum dimension of at least 7.4 Å, as described by Frilette et al. in *J. Catalysis* 67,218-222 (1981). See also Chen et al. *Shape-Selective Catalysis in Industrial Applications*, (Chemical industries;

Vol. 36) Marcel Dekker Inc., New York 1989, ISBN 0-8247-7856-1 and Hoelderich et al. Anqew. Chem. Int. Ed. Engl. 27 226–246 (1988), especially pp.226–229. The large pore size zeolites may also be characterised by a "Constraint Index" of not more than 2, in most cases not more than 1. Zeolite beta, a zeolite having a structure characterised by twelve-membered pore openings, is included in this class of zeolites although under certain circumstances it has a Constraint Index approaching the upper limit of 2 which is usually characteristic of this class of zeolites. The method for determining Constraint Index is described in U. S. Pat. No. 4,016,218, together with values for typical zeolites and of the significance of the Index in U.S. Pat. No.4,861,932, to which reference is made for a description of the test procedure and its interpretation.

Zeolites whose structure is that of a ten membered oxygen ring, generally regarded as the intermediate pore size zeolites may also be effective catalysts for this alkylation reaction if their structure is not too highly constrained. Thus, zeolites such as ZSM-12 (Constraint Index 2) may be effective catalysts for this reaction. The zeolite identified as MCM-22 is a useful catalyst for this reaction. MCM-22 is described in U.S. Pat. No. Application Ser. No. 07/254524, filed 6 Oct. 1988 and also in International Patent Application PCT/US 88/04251, to which reference is made for a description of this zeolite. Thus, zeolites having a Constraint Index up to about 3 will generally be found to be useful catalysts, although the activity may be found to be dependent on the choice of alkylating agent, especially its chain length, a factor which imposes diffusion limitations upon the choice of zeolite.

A highly useful zeolite for the production of the mono-alkylated naphthalenes is zeolite Y in the ultrastable form, usually referred to as USY. When this material contains hydrated cations, it catalyses the alkylation in good yields with excellent selectivity. Zeolite USY is a material of commerce, available in large quantities as a catalyst for the cracking of petroleum. It is produced by the stabilisation of zeolite Y by a procedure of repeated ammonium exchange and controlled steaming. Processes for the production of zeolite USY are described in U.S. Pat. Nos. 3,402,966 (McDaniel), 3,923,192 (Maher) and 3,449,070 (McDaniel); see also Wojciechowski, Catalvtic Crackino. Catalysts. Chemistry and Kinetics. (Chemical Industries Vol. 25), Marcel Dekker, New York, 1986, ISBN 0-8247-7503-8, to which reference is made for a description of zeolite USY, its preparation and properties.

The selected zeolite catalyst contains a cation which has a radius of at least 2.5 Å, and preferably at least 3.0 Å. A number of cations conform to this requirement, including the hydrated cations of a number of metals, including monovalent, divalent and polyvalent, transitional and non-transitional metals. Even though the non-hydrated cations may not themselves conform to the ionic size requirement, the hydrated forms of the cations may do so. In particular, the relatively small radius cations of the alkali metals such as sodium and lithium (ionic radii of 0.95 and 0.60 Å, respectively) do not conform to the requirement, but the hydrated forms of these cations readily meet the requirement (radii of 3.58 and 3.82 Å). In this respect, it is noteworthy that the more intense electric fields surrounding the smaller size non-hydrated cations produce a more intense polarisation of the water molecules so that the radii of the hydrated cations are greater; this effect is readily observed in the case of the sodium and lithium cations, whose hydrated and non-hydrated radii are noted above. A variety of cationic forms of the zeolite may therefore be used. Typical cations which may be used include the hydrated cations of metals of Group IA of the Periodic Table (IUPAC Table), especially sodium or potassium, divalent cations, especially of Group IIA e.g. calcium, and cations of the Rare Earths e.g. cerium, yttrium, lanthanum. The hydrated ammonium cation is also a suitable cationic form of the zeolite and is often preferred for zeolite Y or USY since these zeolites may be commercially available in the ammonium form as a precursor of the decationised or hydrogen form of the zeolite. The hydrated protonic form of the zeolite i.e. where the cation is the hydronium ion $H_3O$, is also effective as a catalyst.

Cations of the required radius may also be provided by various organic species, especially the organic nitrogenous bases. A preferred class of cations of this type are the substituted ammonium cations, for example, alkylammonium cations, especially the short chain alkylammonium cations e.g. tetramethylammonium (TMA), tetraethylammonium (TEA) or tetrapropylammonium (TPA). Short chain alkyl groups up to about $C_6$ are generally useful for cations of this kind.

The ionic radii of selected cations in the hydrated and non-hydrated forms are given below in Table 1.

TABLE 1

| | Cationic Radii (Å) | |
|---|---|---|
| | Ionic Radius (Å) | Hydrated Radius (Å) |
| Monovalent | | |
| H | <0.50 | — |
| $H_3O$ | 1.50 | 2.82 |
| Cs | 1.69 | 3.29 |
| $NH_4$ | 1.48 | 3.31 |
| K | 1.33 | 3.31 |
| Ag | 1.26 | 3.41 |
| Na | 0.95 | 3.58 |
| Li | 0.60 | 3.82 |
| TMA | 3.20 | 3.20 |
| TEA | 3.95 | 3.95 |
| TPA | 4.50 | 4.50 |
| Divalent | | |
| Ca | 0.99 | 4.2 |
| Mg | 0.65 | 4.4 |
| Cu | 0.72 | 4.2 |
| Zn | 0.74 | 4.3 |
| Ni | 0.70 | 4.04 |
| $Pt(NH_3)_4$ | — | >3 |
| Trivalent | | |
| La | 1.15 | 4.52 |

From the Table above it can be seen that hydrated cations will generally conform to the ionic size requirement, even if the non-hydrated form of the cation does not. Thus, for example, the non-hydrated forms of the alkali metal and hydronium cations are too small for the present purposes but when hydrated, the ionic radii increase to a value which is sufficient to achieve the desired increases in alkylation selectivity and activity.

If the zeolite is not already in the desired ionic form, the cation may be introduced by ion-exchange in the conventional manner using a solution of the exchanging cation. The use of an aqueous solution for the ion exchange results in the ion being in the hydrated form after the exchange is complete. Non-hydrated cations may be converted to the hydrated form by exposing the zeolite to hydrating conditions.

Since the improvements in catalytic function are related to the presence of the cations of the required ionic size in the zeolite catalyst, the cations should be present in the zeolite in a sufficient amount to achieve the desired effect. It is not essential for the cation exchange may not be complete for the improvements to be obtained and generally, a single cation exchange procedure should be sufficient to achieve the desired improvements.

The presence of the bulky, cations in the zeolite is thought to selectively block off the interior channels in the zeolite so that production of more highly alkylated species above the mono-alkylated naphthalenes is effectively prevented, either by product size exclusion or spatiospecificity, as described by Chen et al. In any event, the selectivity of the large pore zeolite catalyst is altered notably towards production of the mono-alkylated naphthalene, as compared to the characteristic mixture of various alkylated species obtained with the unmodified zeolite in the hydrogen form. The zeolite may be composited with a matrix material or binder which is resistant to the temperatures and other conditions employed in the alkylation process. Such materials include active and inactive materials and synthetic or naturally occurring zeolites as well as inorganic materials such as clays, silica and/or metal oxides such as alumina, silica or silica-alumina. The latter may be either naturally occurring or in the form of gelatinous precipitates or gels including mixtures of silica and metal oxides. Use of an active material in conjunction with the zeolite may change the conversion and/or selectivity of the catalyst. Inactive materials suitably serve as diluents to control the amount of conversion so that alkylation products can be obtained economically and orderly without employing other means for controlling the rate of reaction. Binders which may be incorporated to improve the crush strength and other physically properties of the catalyst under commercial alkylation operating conditions include naturally occurring clays, e.g., bentonite and kaolin as well as the oxides referred to above.

The relative proportions of zeolite, present in finely divided crystalline form oxide matrix may vary widely, with the crystalline zeolite content ranging from about 1 to about 90 percent by weight and more usually, particularly when the composite is prepared in the form of beads, in the range of about 2 to about 80 weight percent of the composite.

The stability of the alkylation catalyst of the invention may be increased by steaming. U.S. Pat. Nos. 4,663,492; 4,594,146; 4,522,929; and 4,429,176, describe conditions for the steam stabilization of zeolite catalysts which can be utilized to steam-stabilize the catalyst. The steam stabilization conditions include contacting the catalyst with, e.g., 5-100% steam at a temperature of at least about 300 C (e.g., 300-650 C.) for at least one hour (e.g., 1-200 hours) at a pressure of 100-2,500 kPa, e.g. steaming with 75-100% steam at 315°-500° C. and atmospheric pressure for 2-25 hours. The steam stabilization treatment may, as described in the above-mentioned patents, take place under conditions sufficient to initially increase the Alpha Value of the catalyst, and produce a steamed catalyst having a peak Alpha Value. If desired, steaming can be continued to subsequently reduce the Alpha Value from the peak Alpha Value to an Alpha Value which is substantially the same as the Alpha Value of the unsteamed catalyst.

The alkylation process of this invention is conducted such that the organic reactants, i.e., the alkylatable aromatic compound and the alkylating agent, are brought into contact with the zeolite catalyst in a suitable reaction zone such as, for example, in a flow reactor containing a fixed bed of the catalyst composition, under effective alkylation conditions. Such conditions typically include a temperature of from about 100° C. to about 400° C., a pressure of from about 0.2 to about 250 atmospheres, a feed weight hourly space velocity (WHSV) of from about 0.1 $hr^{-1}$ to about 10 $hr^{-1}$ and an alkylatable aromatic compound to alkylating agent mole ratio of from about 0.1:1 to about 50:1, preferably from about 4:1 to about 1:4 e.g. from about 2:1 to about 1:2. The WHSV is based upon the weight of the catalyst composition employed, i.e., the total weight of active catalyst (and binder if present). Preferred reaction conditions include a temperature within the approximate range of from about 100° C. to about 350° C., a pressure of from about 1 about 25 atmospheres, a WHSV of from about 0.5 $hr^{-1}$ to about 5 hr-1 and an alkylatable aromatic compound to alkylating agent mole ratio of from about 0.5:1 to about 5:1. When using naphthalene as the aromatic compound, the pressure should preferably be maintained at a value of at least about 50 psig in order to prevent the naphthalene from subliming into the overhead of the alkylation reactor; the required pressure may be maintained by inert gas pressurization, preferably with nitrogen. The reactants can be in either the vapor phase or the liquid phase and can be neat, i.e., free from intentional admixture or dilution with other material, or they can be brought into contact with the zeolite catalyst composition with the aid of carrier gases or diluents such as, for example, hydrogen or nitrogen. The alkylation can be carried out as a batch-type reaction typically employing a closed, pressurized, stirred reactor with an inert gas blanketing system or in a semi-continuous or continuous operation utilizing a fixed or moving bed catalyst system.

The products comprising alkylated aromatics are characterized by exceptional oxidative and thermal stability. They may be separated from the reaction mixture by stripping off unreacted alkylating agent and naphthalene compound in the conventional manner. It has also been found that the stability of the alkylated product may be improved by filtration over activated charcoal and by alkali treatment to remove impurities, especially acidic by-products formed by oxidation during the course of the reaction. The alkali treatment is preferably carried out by filtration over a solid alkali material, preferably calcium carbonate (lime). In a typical product work-up, it has been found, for example, that the RBOT (Rotating Bomb Oxidation Test, stability can be increased from a value of 184 minutes for an unstripped product ($C_{14}$-alkylnaphthalene) to 290 minutes if the unreacted materials are removed by stripping and to 350 minutes if the stripped product is filtered over lime ($CaCO_3$).

EXAMPLE 1

This Example demonstrates the catalytic activity of a conventional, calcined USY zeolite in H+ form for alkylating naphthalene with a long chain alpha olefin to produce alkylated naphthalene lube base stocks. The catalyst used in this example is an unbound USY catalyst (100% zeolite) containing only about 0:47 wt. percent sodium and having an unit cell size of 24.51 Å (Catalyst A). The alkylation experiment was carried out in a one liter autoclave using 2:1 molar ratio of alpha-C$_{14}$=:naphthalene, 2 wt percent catalyst at 400° F. for 6 hours under a nitrogen pressure of 1 atmosphere. After decanting and filtering the catalyst, the total liquid product was then vacuum distilled at 600° F. to obtain 26 wt percent alkylated lube base stock comprising 85% mono-, 8% di-alkylated naphthalenes, and in addition, 7% olefin dimer due to olefin oligomerization. This corresponds to the conversion of 38 wt percent naphthalene and 22 wt percent alpha C$_{14}$ olefin

EXAMPLE 2

In this Example, the alkylation reaction was carried out under identical conditions as in Example 1 except the USY catalyst loading was increased from 2 to 5 wt percent. As expected, the conversion increases with a higher zeolite loading. The production of alkylated naphthalene lube increases from 26 wt percent (Example 1) to 54 wt percent when the zeolite loading increases from 2 to 5 w percent. Table 1 compares the product selectivity and catalyst activity as a function of zeolite loading.

TABLE 1

| Example No | 1 | 2 |
|---|---|---|
| USY Zeolite, wt. pct. | 2 | 5 |
| Conversion, wt. pct.: | | |
| Naphthalene | 38 | 83 |
| Alpha C$_{14}$ Olefin | 22 | 45 |
| Total Alkylated Lube, wt. pct. | 26 | 54 |
| Product Distribution, wt. pct.: | | |
| Mono-Alkylated | 85 | 80 |
| Di-Alkylated | 8 | 17 |
| Dimer | 7 | 3 |

As the conversion of reactants increases, the product selectivity shifts from mono- to di-alkylated products from 8 percent (Example 1) to 17 percent (Example 2).

EXAMPLE 3

This Example illustrates the catalytic performance of USY zeolite in the hydrated ammonium form. The experiment was carried under identical process conditions as in Example 1 but using a hydrated ammonium USY zeolite instead of the hydrogen form USY (Catalyst A). The hydrated ammonium USY zeolite was obtained from the H$^+$USY by ion-exchanging with a solution of ammonium nitrate as follows: H$^+$USY zeolite (Catalyst A) was slurried with 0.5 N (NH$_4$)$_2$SO$_4$, 5 ml of solution per gram of zeolite. After 1 hour stirring was stopped and solids were allowed to settle. The liquid was then decanted and the exchange procedure repeated. After the second exchange, the zeolite was washed with deionized water until sulfate-free and then dried at 250° F. The resulting hydrated ammonium catalyst contains 0.32 wt. percent sodium and 0.47 wt. percent nitrogen (Catalyst B). Table 2 compares the alkylation performance of USY catalyst in the hydrated ammonium form with the unhydrated hydrogen form.

TABLE 2

| Example No | 1 | 3 |
|---|---|---|
| Catalyst | A | B |
| USY Form | H+ | Hydrated NH$_4$+ |
| Conversion, wt. pct.: | | |
| Naphthalene | 38 | 75 |
| Alpha C$_{14}$ Olefin | 22 | 38 |
| Total Alkylated Lube, wt. pct. | 26 | 47 |
| Product Distribution, wt. pct.: | | |
| Mono-Alkylated | 85 | 92 |

TABLE 2-continued

| Example No | 1 | 3 |
|---|---|---|
| Di-Alkylated | 8 | 8 |
| Dimer | 7 | 0 |

As shown, the conversion of H$^+$ to hydrated NH$_4$+ form USY zeolite increases significantly catalyst activity. The conversion of naphthalene and olefin increase from 38 and 22 to 75 and 38 wt. percent, respectively. Furthermore, even with an increase in conversion, the hydrated ammonium cationic dorm of the USY catalyst provides excellent product selectivity toward mono-alkylated products in comparison with Example 2 (from 85 to 92 percent). In addition, the presence of larger hydrated ammonium cation completely suppresses olefin oligomerization as shown by the disappearance of olefin dimers.

EXAMPLE 4

In this Example, the experiment was carried out under identical conditions as in Example 3 but using a hydrated sodium USY instead of hydrated ammonium USY. The hydrated sodium catalyst contains about 2.4 wt. percent Na (Catalyst C). Table 3 shows that in comparison with the hydrated ammonium catalyst, the hydrated Na$^+$USY catalyst further improves alkylation activity as shown by an increase in total alkylated yield from 47 to 62 wt. percent with an excellent mono-alkylated product selectivity with little dimer formation. The observed improvement is correlated with the larger ionic dimension of the hydrated Na+ cation as shown in Table 3, which also shows that the larger hydrated ionic radii are associated with cations of smaller radius in the non-hydrated form.

TABLE 3

| Example No | 1 | 3 | 4 |
|---|---|---|---|
| Cationic Form | H+ | NH$_4$+ | Na+ |
| Ionic Radii, Å | <0.5 | 1.48 | 0.95 |
| Hydrated Radii, Å | — | 3.31 | 3.58 |
| Conversion, wt. pct.: | | | |
| Naphthalene | 38 | 75 | 96 |
| Alpha Olefin | 22 | 38 | 51 |
| Alkylated Lube, wt. pct. | 26 | 47 | 62 |
| Product Distribution, wt. pct.: | | | |
| Mono-alkylated | 85 | 92 | 89 |
| Di-Alkylated | 8 | 8 | 10 |
| Dimer | 7 | 0 | 1 |

The following Examples demonstrate that the improvement in aromatic alkylation activity and mono-alkylated product selectivity by modification with larger size cations is also observed with a bound USY catalyst containing a support such as alumina, silica or a clay.

EXAMPLE 5

The alkylation experiment was carried out under identical process conditions as in Example 1. As an example, a commercially available USY catalyst was evaluated in this experiment. The catalyst is an FCC catalyst containing approximately 40 wt% USY component with an unit cell size of 24.55 Å. This particular FCC USY catalyst (Catalyst D) is in hydrated ammonium form containing about 0.20 wt. percent Na and 0.90 wt. percent N in ammonium form. About 5 wt. percent of this FCC USY catalyst was used in this Example. The alkylation performance of this catalyst is tabulated in Table 4.

EXAMPLE 6

In this Example, the hydrated ammonium USY catalyst (Catalyst D) was converted to H+USY by calcining at 1000° F. for 24 hours in air. The resulting catalyst (Catalyst E) contains 0.24 wt. percent Na and has an alpha value of 133 and 24.27 Å unit cell size. Table 4 summarizes the performance of this calcined catalyst evaluated under identical process conditions as in Example 5.

EXAMPLE 7

The calcined USY catalyst (Catalyst E) obtained from Example 6 was converted to $H_3O+$ form by hydrating the catalyst with water vapor for four days to saturation point. This hydronium cation USY catalyst (Catalyst F) was evaluated under identical conditions as in Example 5. The results are summarized in Table 4.

EXAMPLE 8

The calcined USY catalyst (Catalyst E) was steamed at 1450° F. for 10 hours in a 45% steam, 55% air atmosphere at 0 psig to reduce the the catalyst acidity from 133 to 2 alpha. The performance of the steamed USY (Catalyst G) is shown in Table 4.

EXAMPLE 9

The hydrated $NH_4^{30}$ USY catalyst (Catalyst D) was modified to hydrated Na+USY by back ion exchanging with a 1N NaCl solution using a procedure very similar to that in Example 3. The resulted catalyst contains about 1.4 wt. percent Na (Catalyst H). Table 4 shows the catalyst performance for naphthalene alkylation.

EXAMPLE 10

The hydrated $NH_4^{30}$ USY catalyst was converted to hydrated K+USY by ion back-exchanging with a 1N $KNO_3$ solution using a procedure similar to that in Example 3. The resulted catalyst contains 2.4 wt. percent K+(Catalyst J). The catalyst performance for naphthalene alkylation is shown in Table 4.

selectivity towards poly-alkylated production. The H+USY catalyst shows a decrease in naphthalene conversion (79 wt. percent) coupled with an increase in olefin conversion (65 wt. percent). This corresponds to the formation of di- and tri-alkylated naphthalene products, resulting an increase in the viscosity of alkylated naphthalene lube base stocks. The steamed catalyst (Catalyst G) shows further increase in tri-alkylated naphthalene formation. These results indicate that the product selectivity can be effectively controlled by modifying the zeolite catalyst with cations of appropriate ionic size and that the ionic size requirement can usually be satisfied by the use of hydrated cations.

EXAMPLE 11

The product properties of alkylated naphthalene lube base stocks produced from various USY catalysts are shown in the following Table 5.

TABLE 5

| Example No | 5 | 6 | 8 |
|---|---|---|---|
| Catalyst | D | E | G |
| USY Form | Hydrated $NH_4$ | Calcined H+ | Steamed H+ |
| Product Properties: | | | |
| Pour Point, °F. | −65 | −50 | −40 |
| KV @40° C., cSt | 25.30 | 35.54 | 46.30 |
| @100° C., cSt | 4.32 | 5.68 | 6.97 |
| Viscosity Index | 60 | 97 | 107 |

Table 5 shows that these alkylated naphthalene synthetic lube base stocks have excellent low-temperature fluidity characteristics as indicated by very low pour point products ($< -40°F$.). The lube viscosity index increases along with the lube viscosity as a result of higher poly-alkylated products. These results indicate that by incorporating the bulky cations into the USY catalyst, various viscosity products can be obtained. This illustrates the flexibility of the catalyst system utilizing the cation modification of the zeolite.

Aromatic-containing synthetic lubricants with improved product qualities may be obtained with the use of alkylated naphthalene lube base stocks produced from large-pore zeolite, including USY, in the appropri-

TABLE 4

Effect of Hydrate Cation on Naphthalene Alkylation Performance of USY Catalyst

| Example No | 5 | 6 | 7 | 8 | 9 | 10 |
|---|---|---|---|---|---|---|
| Catalyst | D | E | F | G | H | J |
| USY Form | Hydrated $NH_{4+}$ | Calcined H+ | Hydrated $H_3O+$ | Steamed H+ | Hydrated NA+ | Hydrated K+ |
| Ionic Radii, | 1.48 | <0.5 | 1.50 | <0.5 | 0.95 | 1.33 |
| Hydrated Radii, | 3.31 | — | 2.82 | — | 3.58 | 3.31 |
| Conversion, wt. pct.: | | | | | | |
| Naphthalene | 96 | 79 | 63 | 79 | 96 | 100 |
| Alpha Olefin | 54 | 65 | 41 | 68 | 57 | 59 |
| Total Alkylated Lube, wt. pct. | 64 | 68 | 46 | 71 | 66 | 68 |
| Product Distribution, wt. pct.: | | | | | | |
| Mono-Alkylated | 83 | 46 | 70 | 38 | 82 | 81 |
| Di-Alkylated | 14 | 34 | 24 | 38 | 12 | 12 |
| Tri-Alkylated | — | 7 | — | 15 | — | — |
| Dimer | 3 | 13 | 6 | 9 | 6 | 7 |

The results summarized in Table 4 indicate that all USY zeolites containing hydrated cations of the requisite ionic radii (Catalysts D, H and J) provide nearly complete conversion of naphthalene (>96 wt. percent) and very high selectivity for mono-alkylated naphthalene production (>86 percent). The conversion of hydrated $NH_4^{30}$ (Catalyst D, Example 5) to H+form (Catalyst E, Example 6) by calcination shifts the product ate cationic form. Modification of the zeolite alkylation catalyst by incorporating bulky cations, preferably in the form of hydrated cations, can effectively control the degree of alkyl substitution and, by so doing, alter the final lube viscosity. In addition, the presence of the cations of the requisite size improves catalyst activity and stability, thus improving overall naphthalene alkylation process economics.

We Claim::

1. A process for preparing long chain alkyl substituted naphthalenes which comprises reacting a naphthalene with an alkylating agent possessing an alkylating aliphatic group having at least six carbon atoms under alkylation reaction conditions and in the presence of an alkylation catalyst comprising a porous crystalline zeolite containing cations having a radius of at least 2.50 Å, to form an alkylated naphthalene possessing at least one alkyl group derived from the alkylating agent.

2. A process according to claim 1 in which the zeolite is a large pore size zeolite having pores with a minimum dimension of at least 7.4 Å.

3. A process according to claim 1 in which the zeolite has a Constraint Index of not more than 2.

4. A process according to claim 3 in which the zeolite has a Constraint Index of not more than 1.

5. A process according to claim 1 in which the zeolite comprises zeolite X or zeolite Y.

6. A process according to claim 5 in which the zeolite comprises zeolite USY.

7. A process according to claim 1 in which the cations have a radius of at least 3.0 Å.

8. A process according to claim 1 in which the cations comprise hydrated cations.

9. A process according to claim 8 in which the hydrated cations comprise hydrated cations of an alkali metal.

10. A process according to claim 8 in which the alkali metal comprises sodium or potassium.

11. A process according to claim 8 in which the hydrated cations comprise hydrated ammonium cations.

12. A process according to claim 8 in which the hydrated cations comprise hydrated hydronium cations.

13. A process according to claim 1 in which the alkylating aliphatic group contains at least about 8 carbon atoms.

14. A process according to claim 13 in which the alkylating aliphatic group contains at least about 12 carbon atoms.

15. A process according to claim 14 in which the alkylating aliphatic group contains from 14 to 20 carbon atoms.

16. A process according to claim 1 in which the alkylating agent comprises an olefin.

17. A process according to claim 1 in which the alkylation reaction conditions include a temperature of from about 100° C. to about 400° C., a pressure of from about 0.2 to about 25 atmospheres, an WHSV of from about 0.1 to 10 and an alkylatable aromatic compound to alkylating agent mole ratio of from about 0.1:1 to 50:1.

18. A process according to claim 17 in which the alkylation reaction conditions include a temperature of from about 100° C. to 300° C., a pressure of from about 1 to about 5 atmospheres, a WHSV of from about 0.5 to about 5 and an alkylatable aromatic compound to alkylating agent mole ratio of from about 5:1 to about 5:1.

19. A process for preparing long chain alkyl substituted naphthalenes which comprises reacting naphthalene with a olefin containing at least 8 carbon atoms as an alkylating agent under alkylation reaction conditions and in the presence of an alkylation catalyst comprising a porous crystalline zeolite containing hydrated cations, to form an alkylated naphthalene possessing at least one alkyl group derived from the alkylating agent.

20. A process according to claim 19 in which the zeolite is a large pore size zeolite having a minimum pore dimension of at least 7.4 Å.

21. A process for preparing long chain alkyl substituted naphthalenes which comprises reacting naphthalene with a olefin containing from about 12 to about 20 carbon atoms as an alkylating agent under alkylation reaction conditions and in the presence of an alkylation catalyst comprising a porous crystalline zeoline having a minimum pore dimension of at least 7.4 Å and the crystal structure of zeolite Y and containing hydrated cations, to form an alkylated naphthalene possessing at least one alkyl group derived from the alkylated agent.

22. A process according to claim 21 in which the hydrated cations comprise hydrated cations of an alkali metal.

23. A process according to claim 21 in which the cations comprise hydrated ammonium cations.

24. A process according to claim 21 in which the cations comprise hydrated cations which have a radius of at least 3.0 Å.

25. A process according to claim 21 in which the zeolite is zeolite USY.

26. A process according to claim 20 in which the alkylation is carried out under an inert gas in a bath reactor in which pressure is maintained at a value of at least 50 psig.

27. A process according to claim 20 in which the alkylated naphthalene is contacted with an alkali to remove acidic by-products.

* * * * *